United States Patent
Liu et al.

(10) Patent No.: US 9,915,630 B2
(45) Date of Patent: Mar. 13, 2018

(54) BIOCHIP WITH BIOSENSORS AND FLUIDIC DEVICES

(71) Applicant: TAIWAN SEMICONDUCTOR MANUFACTURING COMPANY, LTD., Hsinchu (TW)

(72) Inventors: Yi-Shao Liu, Zhubei (TW); Chun-Wen Cheng, Zhubei (TW); Chun-Ren Cheng, Hsinchu (TW)

(73) Assignee: TAIWAN SEMICONDUCTOR MANUFACTURING COMPANY, LTD., Hsinchu (TW)

( * ) Notice: Subject to any disclaimer, the term of this patent is extended or adjusted under 35 U.S.C. 154(b) by 55 days.

(21) Appl. No.: 14/603,925

(22) Filed: Jan. 23, 2015

(65) Prior Publication Data

US 2015/0139857 A1    May 21, 2015

Related U.S. Application Data

(63) Continuation of application No. 13/838,905, filed on Mar. 15, 2013, now Pat. No. 8,951,716.

(51) Int. Cl.
| | |
|---|---|
| *G01N 21/75* | (2006.01) |
| *G01N 27/414* | (2006.01) |
| *G03F 7/20* | (2006.01) |
| *B01L 3/00* | (2006.01) |
| *G01N 33/543* | (2006.01) |
| *G03F 7/00* | (2006.01) |

(52) U.S. Cl.
CPC .... *G01N 27/4145* (2013.01); *B01L 3/502715* (2013.01); *G01N 33/54373* (2013.01); *G03F 7/0035* (2013.01); *G03F 7/20* (2013.01); *B01L 3/502707* (2013.01); *B01L 2200/12* (2013.01); *B01L 2300/0636* (2013.01); *B01L 2300/0645* (2013.01); *B01L 2300/0819* (2013.01); *B01L 2300/0887* (2013.01)

(58) Field of Classification Search
CPC .......... G01N 27/4145; G01N 33/54373; G03F 7/0035; G03F 7/20; B01L 3/502715; B01L 3/502707; B01L 2300/0887; B01L 2300/0645; B01L 2200/12; B01L 2300/0819; B01L 2300/0636
See application file for complete search history.

(56) References Cited

PUBLICATIONS

Leichle, Thierry et al., "Biosensor-Compatible Encapsulation for Pre-Functionalized Nanofluidic Channels Using Asymmetric Plasma Treatment", Sensors and Actuators B 161 (2012) 805-810.
U.S. Appl. No. 13/706,002, filed Dec. 5, 2012, Liu et al.

*Primary Examiner* — Dennis White
(74) *Attorney, Agent, or Firm* — Hauptman Ham, LLP

(57) ABSTRACT

A biochip includes a substrate, where the substrate includes at least one hole extending from a first surface of the substrate to a second surface of the substrate opposite the first surface, and where the substrate comprises a microfluidic channel pattern. The biochip further includes a surface modification layer over the substrate. Additionally, the biochip includes a sensing wafer bonded to the substrate, where the sensing wafer has one or more modified surface patterns having different surface properties from each other.

20 Claims, 9 Drawing Sheets

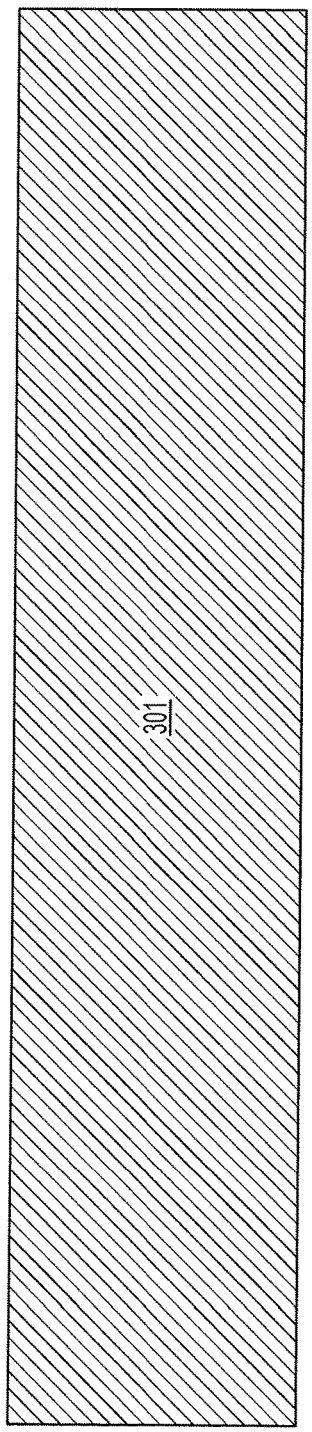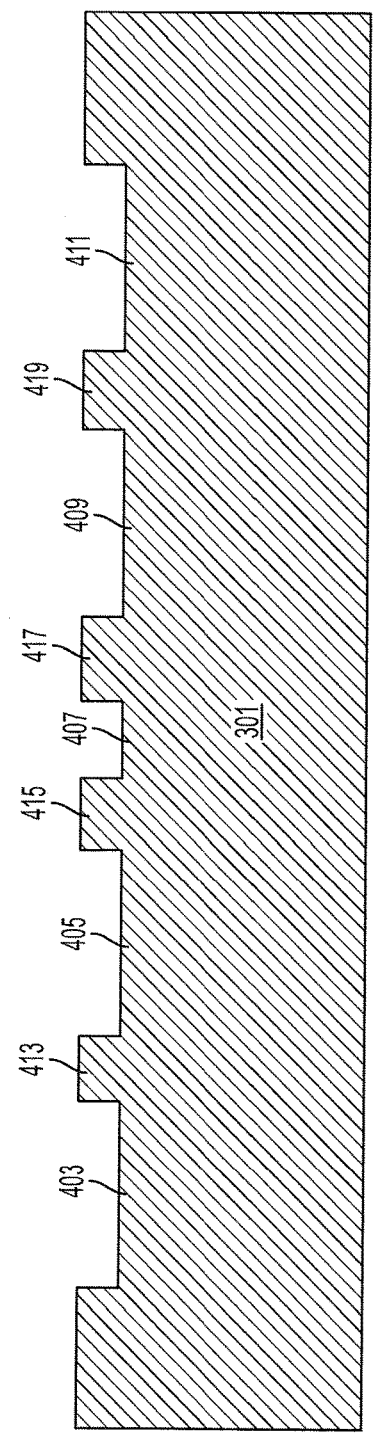

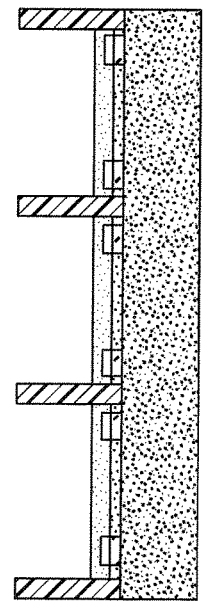
FIG. 11A
FIG. 11B
FIG. 11C
FIG. 11D
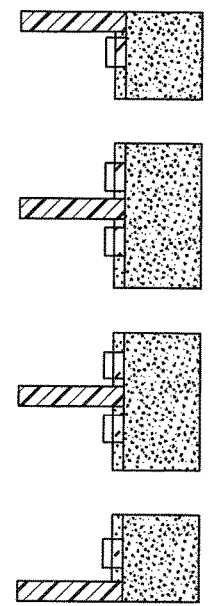
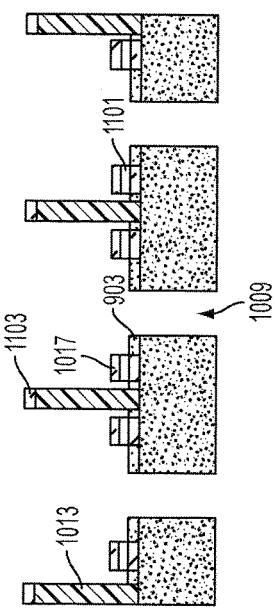
FIG. 11E
FIG. 11F
FIG. 11G

BIOCHIP WITH BIOSENSORS AND FLUIDIC DEVICES

PRIORITY CLAIM

The present application is a continuation of U.S. application Ser. No. 13/838,905, filed Mar. 15, 2013, the disclosure of which is incorporated herein in its entirety.

FIELD

This disclosure relates to biochips. Particularly, this disclosure relates to biochips having biosensors and fluidic devices.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection of biomolecules can be performed by detecting the bio-entities or the biomolecules themselves, or through interaction and reaction between specified reactants and bio-entities/biomolecules. Such biosensors can be manufactured using semiconductor fabrication processes, can quickly convert electric signals, and can be easily applied to integrated circuits (ICs) and microelectromechanical systems (MEMS).

Biochips are essentially miniaturized laboratories that can perform hundreds or thousands of simultaneous biochemical reactions. Biochips can detect particular biomolecules, measure their properties, process sensed signals, and may even analyze the corresponding+data directly. Biochips enable researchers to quickly screen large numbers of biological analytes for a variety of purposes, from disease diagnosis to detection of bioterrorism agents. Advanced biochips use a number of biosensors along with fluidic channels to integrate reaction, sensing and sample management. While biochips are advantageous in many respects, challenges in their fabrication and/or operation arise, for example, due to compatibility issues between the semiconductor fabrication processes, the biological applications, and restrictions and/or limits on the semiconductor fabrication processes.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIGS. 3-5, 6A-6B, and 7 are cross-sectional views of partially fabricated biochip devices constructed according to one or more steps of the methods of FIG. 2A according to one or more embodiments of the present disclosure.

FIGS. 8-9, 10A-10I, and 11A-11G are cross-sectional views of partially fabricated biochip devices constructed according to one or more steps of the method of FIG. 2B according to one or more embodiments of the present disclosure.

DETAILED DESCRIPTION

Figure 1:
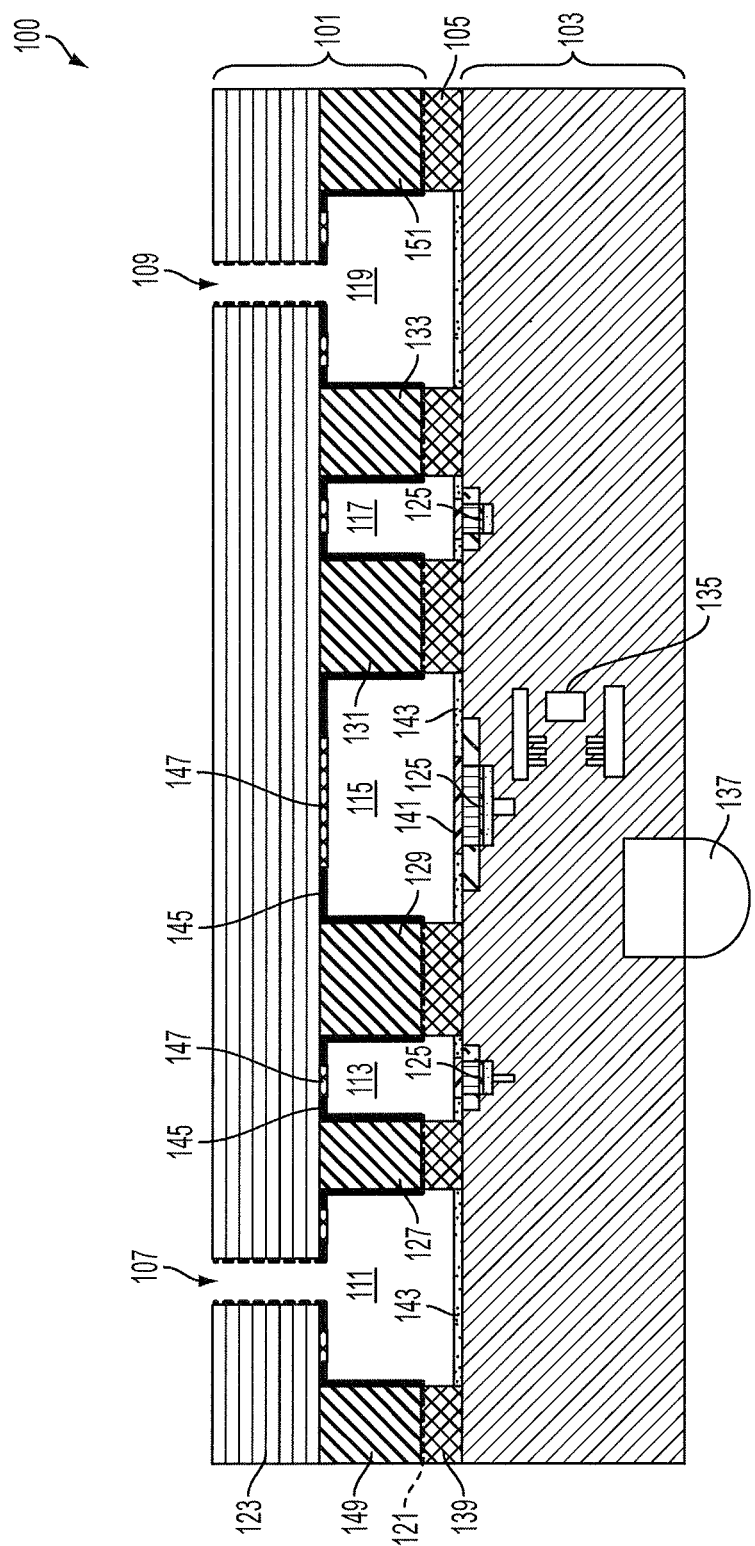
FIG. 1 is a cross-sectional view of a biochip in accordance with various embodiments of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

Some biochips involves various bioreceptors which react with various biological material of interest in one or more wells. One approach is to tag a reaction with a fluorescent or phosphorescent bioreceptor that emits a detectible photon. A coordinated approach would encode the sensor to a location on the biochip, so that a positive reaction and photodetection would be correlated to the location to determine the nature of the reaction, for example, identity of the biological material. The signal may be optical, magnetic, electrical or a mass-sensitive measurement such as surface acoustic wave or microbalance weights. A random approach is to encode the sensor with different fluorescence, phosphorescence, or otherwise detectible and differentiable sensors. A positive detection would be correlated to the type of signal transduced to determine the nature of the detection. The signal transduced may be photons, for example, a different wavelength light is generated for different biological materials or surface plasmon resonance.

More advanced biochips involve not only biosensors, but also various fluidic channels to deliver biological material to the sensors. The fluidic channels may be a part of a microfluidic system that includes pumps, valves, and various measurement devices such as flow meters, pressure transducers, and temperature sensors. Because a biochip combines electrical processing and fluid processing, fluid handling ability has to successfully integrate within a semiconductor chip environment. A potential use of biochips is as a lab-on-a-chip—where medical professionals can use a small biochip to perform testing in the field, obtain results contemporaneously, and proceed with treatment or further analysis without retreating to a laboratory. Especially for medical professionals working in remote areas where sample preservation may be difficult, lab-on-a-chip devices can save lots of time spent traveling and waiting. These lab-on-a-chip devices are often single-use, or disposable, devices. As such, the manufacturing costs have to be low to be economically viable.

Semiconductor processing often involves baking, curing, and exposing various surfaces to plasma energy and radiation energy. At high temperatures (i.e., above about 75 degrees Celsius) and/or high energies, these processes would damage or destroy bioreceptors and surface modification layers, which usually are delicate bio-molecules or very thin layers of surface chemistry. For example, the bioreceptors may be antibodies/antigens, enzymes, nucleic acids/DNA, cellular structures/cells, and biomimetic receptors. The surface modification chemistry may include thin layers (one or two molecules thin) of hexamethyldisilazane (HMDS), 3-aminopropyl triethoxysilane (APTES), agar, or hydrogel.

Thus, the bio-functionalization of surfaces when biomolecules are attached, are often performed after all the semiconductor processes are completed. In some designs, the fluidic channels are formed directly on the semiconductor substrate, usually silicon wafer, along with the biosensors. In other designs, the fluidic channels are formed on a fluidic substrate that is subsequently bonded to the sensing wafer with the biosensors. The fluidic channel formation, usually etching a trench or via into the substrate, can damage the biosensors, bioreceptors or surface modification layer. When a high temperature bonding process is used, the bioreceptors are deposited on the interior walls of the fluidic channels after the bonding process and the fluidic channels are enclosed, usually by flowing through each biochip a high concentration of bioreceptors through the fluidic channel surfaces having some affinity for the bioreceptors. However, the density of bioreceptors is hard to control and the process is slow and wasteful of bioreceptors and reagents. In some cases, the bound-bioreceptor density varies throughout the biochip or a batch of biochips (not uniform) as the concentrations in the reagents change. The process may be limited to a single type of bioreceptors because there the flow surfaces cannot be easily patterned after the substrates are bonded and thus multiple detections are limited to the random approach discussed above. For these reasons, the process is costly and disposable units are not economically viable.

The various embodiments of the present disclosure contemplate a wafer-level process and a biochip that allows surface chemistry and/or bio-functionalization to occur before the bonding of the fluidic substrate and the sensing wafer at about room temperature without damaging the exposed surfaces with high temperature, high energy semiconductor fabrication processes. The use of two substrates—the fluidic substrate and the sensing wafer substrate-introduces flexibility in the choice of bonding material because one of the substrates may be designed to hold the more delicate bio-materials and the other substrate may be exposed to semiconductor processes that may otherwise damage the delicate bio-materials. The fluidic substrate includes microfluidic channels and inlets/outlets. The fluidic substrate is formed separately from the sensing wafer and total cycle time is reduced. One or more of the various method embodiments of the present disclosure may be performed in a semiconductor fabrication facility and are compatible with the complementary metal-oxide-semiconductor (CMOS) process.

FIG. 1 is a cross-section of a biochip 100 in accordance with various embodiments of the present disclosure. The biochip 100 includes a fluidic substrate 101 and a sensing wafer substrate 103 with a bonding material 105 between. The bonding material 105 is a biologically compatible material that does not react with the analyte, bioreceptors, or any testing fluid. The bonding material may be a photoresist. In one example, the photoresist is polysilsesquioxane (PSQ). In another example, the bonding material is 3-aminopropyl triethoxysilane (APTES). PSQ and APTES are commercially available materials, for example, from Sigma-Aldrich® of St. Louis, Mo.

The fluidic substrate 101 has a fluidic inlet 107 and a fluidic outlet 109 through the fluidic substrate 101. The fluidic substrate 101 has a first surface 121 and a second surface 123. While labeled as inlet and outlet, the flow of 107 and 109 may be reversed. The first surface 121 includes microfluidic channel patterns, shown as channels and wells 111, 113, 115, 117, and 119, referred to herein collectively as cavities. The various cavities 111, 113, 115, 117, and 119 are connected to each other via various pathways and may be different sizes depending on the design of the biochip. Some of the cavities may match a biosensor, providing a well having a sensing surface. Some of the cavities may be a fluidic reservoir. Some of the cavities may include bioreceptors that would react detectibly with an analyte. The features between the cavities on the fluidic substrate 101 are island features, for example, island features 127, 129, 131, and 133. According to various embodiments, the island features 127, 129, 131, and 133 include a flat portion that is bonded to the bonding material 105 and hence through the bonding material 105 to the sensing wafer 103. In some embodiments, the island features 127, 129, 131, and 133 are a portion of the fluidic substrate 101 and the microfluidic channels 111, 113, 115, 117, and 119 are formed by etching into the fluidic substrate 101. In other embodiments, the island features 127, 129, 131, and 133 are formed on the fluidic substrate 101 by depositing and patterning a material or by selectively depositing a material.

The fluidic substrate also includes a first surface modification layer 145. The first surface modification layer 145 conformally covers all of the first surface 121 of the fluidic substrate 101 or a pattern on the first surface 121. In FIG. 1, the first surface modification layer 145 covers all surfaces inside a fluidic channel, for example, channels and wells 111, 113, 115, 117, and 119, with exception of any surface covered by a second surface modification layer 147. The first surface modification layer 145, shown in FIG. 1, may optionally cover the sidewalls of the fluidic inlet and outlet 107/109. The first surface modification layer 145, shown using dotted lines, may also optionally cover a top of the island features 127, 129, 131, and 133 and biochip edges 149 and 151. The biochip edges 149 and 151 include scribe lines from which each die containing a biochip would be separated from each other. The biochip edges 149 and 151 are sufficiently wide such that the biochip remains hermetically sealed between the fluidic substrate 101 and the sensing wafer substrate 103 after dicing.

The first surface modification layer 145 is a bio-compatible material that provides a surface property to facilitate the operation of the biochip. The surface property may be chemical, mechanical, or electrical. For example, the first surface modification layer 145 may provide a hydrophilic, a hydrophobic, or a surface chemistry such as affinity for particular functional groups. According to various embodiments, the first surface modification layer 145 may be hexamethyldisilazane (HMDS), silicon oxide, amino-silane (for example, 3-aminopropyl triethoxysilane (APTES)), certain metal oxides, agar, or—hydrogel (for example, polyethylene glycol (PEG) hydrogel). Patterning of the first surface modification layer 145 may be performed to exclude it at the top of the island features 127, 129, 131, and 133 if the first surface modification layer 145 does not adhere to the bonding material 105. In the example of HMDS, the HMDS renders the first surface 121 hydrophobic. During operation of the biochip, water-based analyte does not adhere to the hydrophobic surface and is directed to the sensing surfaces which may be coated with a hydrophilic material. In other embodiments, a hydrophilic coating is used for another purpose.

The fluidic substrate surface 121 may also include a second surface modification layer 147 that provides a different surface property than the first surface modification layer 145. If used, the second surface modification layer 147 is a different material from the first surface modification layer 145 and may be hexamethyldisilazane (HMDS), silicon oxide, silane, 3-aminopropyl triethoxysilane (APTES), certain metals or metal oxides, agar, or polyethylene glycol (PEG) hydrogel. In some embodiments, the second surface modification layer 147 may be patterned on an externally observable or electrically detectible location on the first surface 121. In some embodiments, the second surface modification layer 147 is used to bind bio-molecules having certain functional groups to specific wells or channels. During biochip operation, the bound bio-molecules can participate in reactions with analyte where either the reaction or result of the reaction is detectible. In some examples, the second surface modification layer 147 may be a metal or compound that has affinity for certain functional groups, i.e. gold or platinum for thiol groups.—Another example is the coating of Poly-L-Lysine on glass or plastic-ware for promotion of cell adhesion. The thicknesses of the first surface modification layer 145 and the second surface modification layer 147 may be different.

The bonding material 105 between the fluidic substrate 101 and the sensing wafer 103 may be any bio-compatible adhesive, glue, polymer, epoxy, bonder, or solder that can provide a hermetic seal between channels and wells. The bonding material 105 is compatible with CMOS processes and may be patterned. The bonding material 105 allows bonding of the fluidic substrate 101 and the sensing wafer at low temperatures, less than about 150 degrees Celsius or less than about 100 degrees Celsius. In one example, the bonding material 105 is poly(phenylmethyl)silsesquioxane (PSQ). PSQ can be patterned like a photoresist using a photolithographic process or printed in a pattern using a jet printer. Once activated using oxygen-containing plasma, PSQ can bond to a silicon containing substrate at room temperature. In another example, the bonding material 105 is 3-aminopropyl triethoxysilane (APTES). APTES can be deposited in vapor phase or printed. Once activated using a catalyst, APTES can covalently bond to a silicon-containing substrate at room temperature. Suitable catalysts include water, toluene, and phosphate buffered saline (PBS) solution.

The sensing wafer 103 includes a patterned sensing surface 139 and one or more biosensors 125. The biosensors 125 may be a biological field-effect transistor (BioFET), an optical sensor (for example, a CMOS sensor), electromagnetic biosensors, electrochemical biosensors, and mechanical sensors (for example, mass sensitive sensors or motion sensitive sensors). The biosensors 125 may sense electrical, optical, or mechanical properties on the sensing surface or in the analyte. Electrical property biosensors measure a voltage potential or electric field. Optical property biosensors measure intensity and wavelength of a light radiation. Mechanical property sensors measure a different electrical or optical value based on difference in mass or motion. Examples include piezoelectric sensors, laser Doppler vibrometers, Hall-effect sensors, and capacitive micromachined ultrasonic transducers. The biosensor 125 is connected through an interconnect structure 135 to one or more electrodes 137. The electrodes 137 provide power and input/output of electrical signals to the biochip. The electrodes 137 may be bumps such as a ball grid array, copper pillars, or solder material. In various embodiments, the electrodes 137 allows a reading of the data collected from the sample and may further allow control of the biological analysis. The biochip 100 may be inserted into a module having corresponding electrode pads that further includes input/output devices and a power supply. Although only three biosensors 125 are depicted in FIG. 1, each of the cavities 111, 113, 115, 117, and 119 may have a corresponding biosensor.

In some embodiments, the biosensor 125 is external to the sensing wafer 103 and only a patterned sensing surface 139 is provided. The presence of analyte and/or reaction is detected externally through the one or more transparent substrates 101 or 103. In such embodiments, the biochip 100 may be inserted into a photodetector which would activate the reaction and analyze the extent or identity of the analyte through a positive photodetection at a coordinate on the biochip 100 or a positive photodetection of a particular type of photon.

As shown in FIG. 1, the patterned sensing surface 139 includes a sensing surface 141 and a passivation layer 143. Each cavity 111, 113, 115, 117, and 119 may include only sensing surface 141 or passivation layer 143, or both. In some embodiments, the sensing surface 141 or the passivation layer 143 is the same material as the first surface modification layer 145 or the second surface modification layer 147.

Figure 2A:
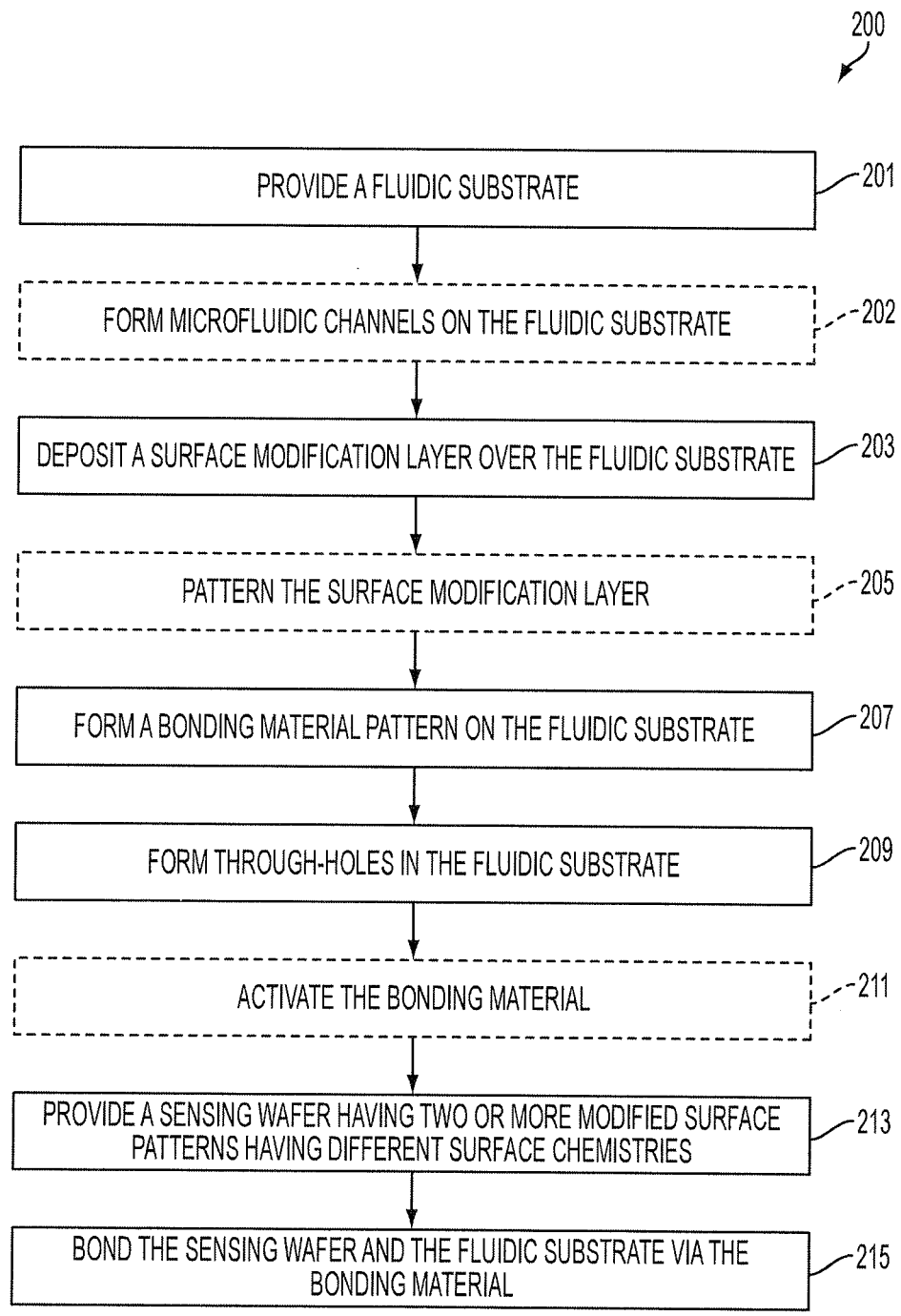
FIGS. 2A-2B are flow charts of various embodiments of methods of fabricating a biochip device according to one or more embodiments of the present disclosure.
Figure 2B:
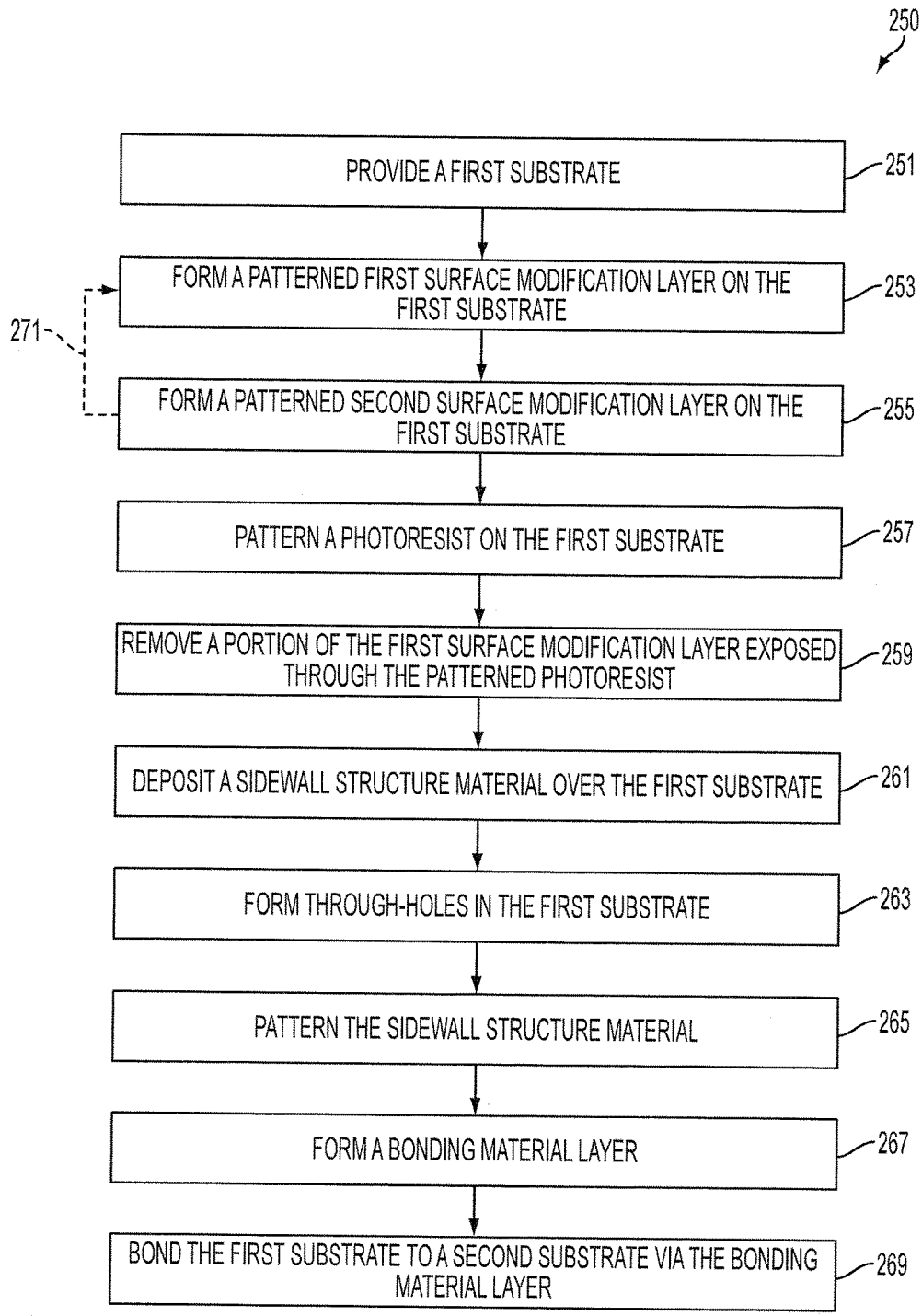

FIGS. 2A and 2B are flow charts of various embodiments of methods of fabricating a biochip device according to one or more aspects of the present disclosure. FIGS. 3-5, 6A-6B, 7-9, 10A-10I, and 11A-11G are cross-sectional views of partially fabricated biochip devices constructed according to one or more steps of the method of FIGS. 2A and 2B. In operation 201 of FIG. 2A, a fluidic substrate is provided. FIG. 3 shows the fluidic substrate 301. The fluidic substrate 301 may be a transparent substrate, including glass or quartz, or opaque, depending on whether the biochip is designed for external photo-detection or inspection. In some embodiments, the fluidic substrate 301 is silicon, sapphire, silicon carbide, or other commonly used semiconductor substrates that does not react with the analyte or solution. According to some embodiments, the fluidic substrate may be at least 100 microns thick or about 700 microns thick.

In operation 202, a microfluidic channel pattern is formed on the fluidic substrate. FIG. 4 shows a fluidic substrate 301 with a microfluidic channel pattern. A microfluidic channel pattern is formed first by patterning a photoresist over the substrate 301. After developing the photoresist and removed portions of the photoresist, the remaining photoresist is used as a etch mask to form the microfluidic channel pattern in the fluidic substrate 301. The microfluidic channels 403, 405, 407, 409, and 411 are etched into the fluidic substrate 301 by wet etch or dry etch. In some embodiments, a dry etch is used to form channels and wells at about 100 nm deep or deeper. Much deeper channels and wells that are microns deep or deeper are formed by wet etch or a combination of wet and dry etches. The various channels and wells connect to each other in a network of microfluidic channels. Other features including pumps, valves, sensors, and other micro-electro-mechanical system (MEMS) devices may be formed or embedded in the fluidic substrate 301. The field regions between the channels and wells 403, 405, 407, 409, and 411 are island features, for example, features 413, 415, 417, and 419. The fluidic substrate 301 will be eventually bonded to a sensing wafer at top of these island features with a bonding material. To avoid leakage between adjacent channels and wells, the bonding material hermetically seals the channels and wells from each other.

In some embodiments, a microfluidic channel pattern is formed on the sensing wafer and not the fluidic substrate. In those embodiments, operation 202 is not performed. In still other embodiments, microfluidic channel patterns are formed in both the fluidic substrate and the sensing wafer.

Figure 5:
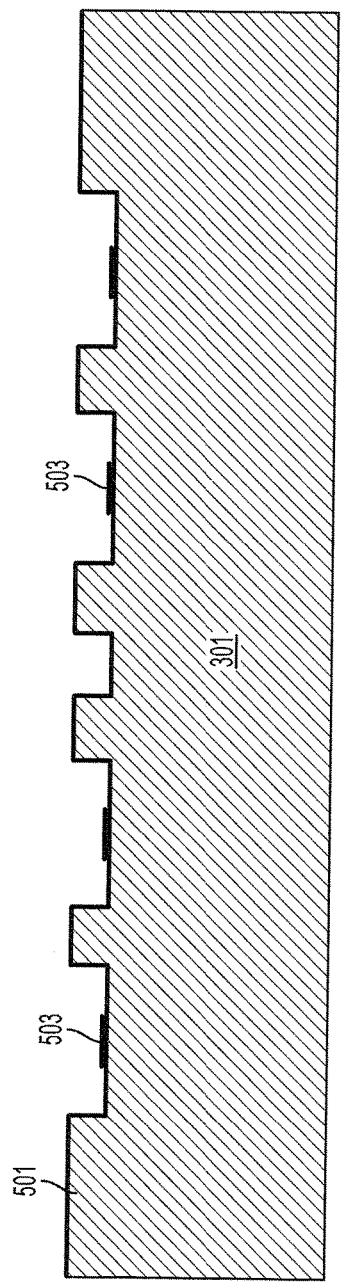

In operation 203 of FIG. 2A, a first surface modification layer is deposited over the microfluidic channel pattern. The first surface modification layer 501 conformally covers the microfluidic channel pattern as shown in FIG. 5, including covering the sidewalls of various wells and channels. The method of depositing the first surface modification layer depends on the material. In one example where HMDS is the first surface modification layer, the HMDS is deposited with a photolithography tool. In another example where APTES is the first surface modification layer, the APTES is deposited by immersing the substrate in a solution containing APTES or by exposing the substrate to an APTES vapor. In other examples, the first surface modification layer 501 may be deposited using a chemical vapor deposition (CVD) method, including an atomic layer deposition (ALD), plasma enhanced chemical vapor deposition (PECVD), spraying, coating (including spin-on deposition), condensing, or printing.

The first surface modification layer may be patterned in optional operation 205. In one embodiment, a photoresist pattern is deposited over the fluidic substrate 301 before the first surface modification layer is deposited. A patterned first surface modification layer remains after the photoresist pattern is removed. In another embodiment, the photoresist pattern is formed after depositing a blanket first surface modification layer. The first surface modification layer is patterned through the patterned photoresist by etching, developing, or other methods of removing. In one example when the first surface modification layer is HMDS, a blanket layer is deposited before depositing a photoresist and patterning the photoresist, then the blanket HMDS is exposed to a solvent that removes the exposed portions of the HMDS through the photoresist pattern but not the portions covered by the photoresist.

In some embodiments, a second surface modification layer pattern is formed on the fluidic substrate using a different method from the first surface modification layer. The second surface modification layer may be formed directly on the first surface modification layer or on an exposed portion of the fluidic substrate. For example, a second surface modification layer is deposited using a printing method directly over a first surface modification layer. The second surface modification layer may have a different density and provide a different surface property from the first surface modification layer. In some embodiments, the second surface modification layer may be deposited by selective deposition. For example, after patterning the hydrophobic HMDS, a hydrophilic material may be selectively deposited on the exposed substrate surface by spraying or coating the substrate as the hydrophilic material would not adhere to a hydrophobic material. FIG. 5 shows the second surface modification layer 503 formed over the first surface modification layer 501 in some microfluidic wells or channels.

Referring to operation 207 of FIG. 2A, a bonding material pattern is formed on the fluidic substrate. The bonding material pattern is used to bond the sensing wafer and the fluidic substrate. According to various embodiments, the bonding material is pattern is formed by printing directly on the fluidic substrate, by a photolithographic process, or by condensing a vapor containing the bonding material on the fluidic substrate. In some embodiments, the bonding material does not interact with the first surface modification layer and it is or fully selectively deposited directly on the first surface modification layer. In the full deposition embodiments, the bonding material may also act as a surface modification layer where it is not bonded to the sensing wafer.

Figure 6A:
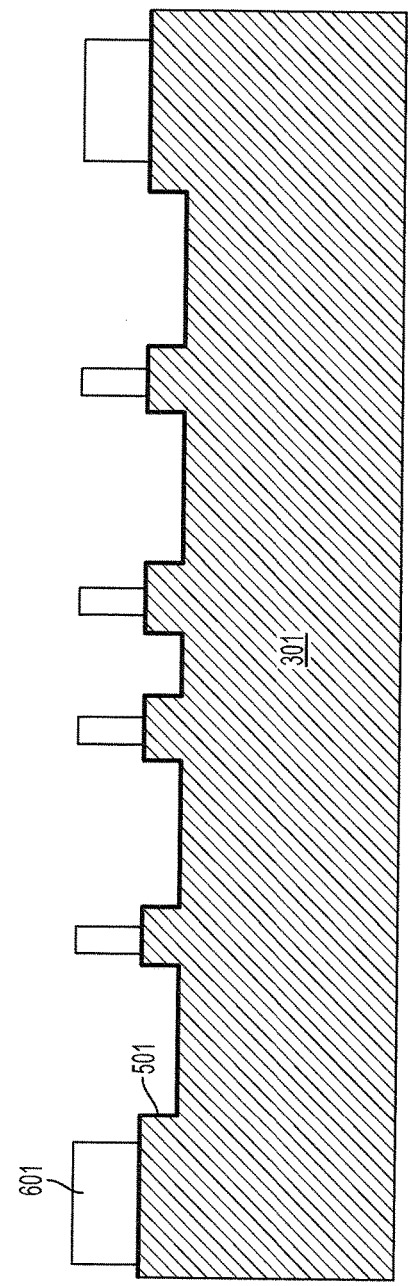

FIG. 6A is a cross-sectional diagram of a fluidic substrate 301 including a bonding material pattern 601 on portions of the first surface modification layer 501. The bonding material acts as barriers between microfluidic channels and also seals the biochip at its edges.

Figure 6B:
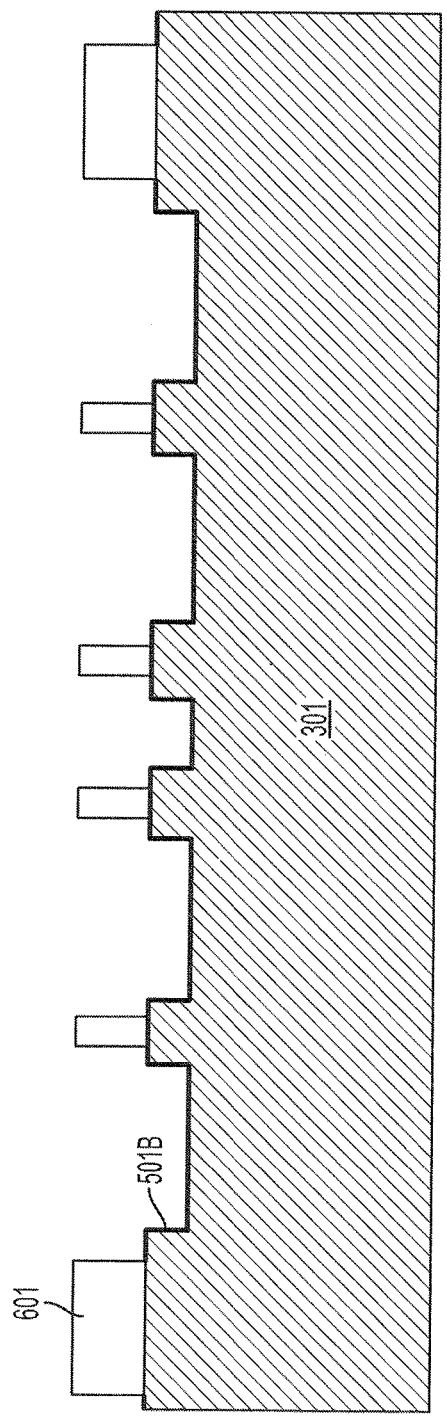

In some embodiments, the bonding material can detrimentally react with the first surface modification layer or the second surface modification layer if used. To avoid such a reaction the bonding material is printed onto exposed fluidic substrate portion and the first surface modification layer is patterned before the bonding material is deposited. FIG. 6B is a cross-sectional diagram of a fluidic substrate 301 including a bonding material pattern 601 on portions of the fluidic substrate 301 without the first surface modification layer 501B. In one example where the first surface modification layer is HMDS, the HMDS may be patterned by photolithography with PR AZ5214-E and developer AZ400K, both of which are commercially available formulations, for example, from Clariant Corporation of Somerville, N.J.

According to various embodiments, the bonding material is a silicon-containing material (for example, a silane) that can be activated to form silanol or dangling bonds that readily bonds silicon or silicon oxide. In one embodiment, the bonding material is a negative photoresist polysilsesquioxane (PSQ). PSQ may be patterned by exposing a portion of it to light radiation. The unexposed portion is soluble to a photoresist developer and washes away during the developing process. PSQ is activated using an oxygen-containing plasma. In another embodiment, the bonding material is APTES, which is deposited by vapor and activated with a liquid or vapor catalyst, including water, toluene, or phosphate buffered saline (PBS) solution.

Figure 7:
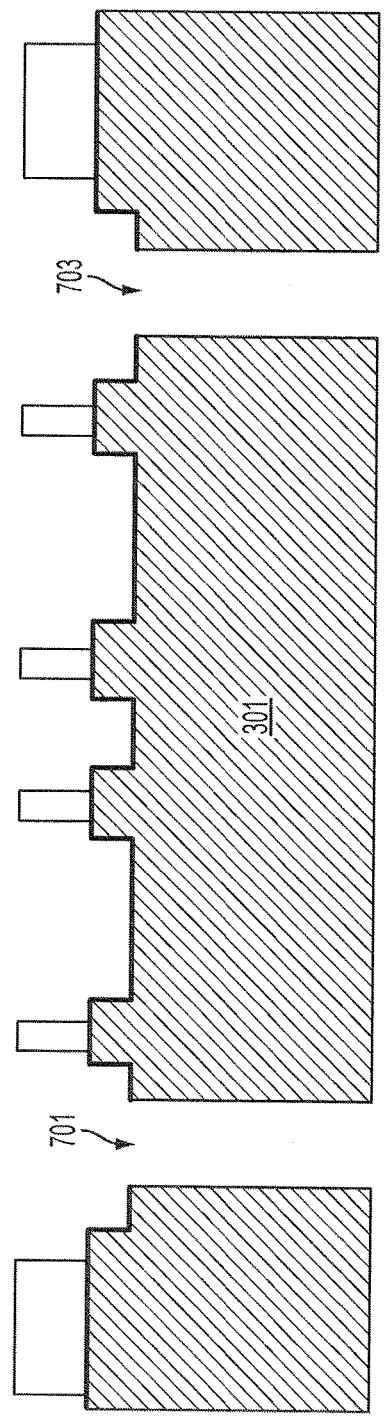

Referring back to FIG. 2A, in operation 209, through-holes are formed in the fluidic substrate. In some embodiments, the through-holes are formed by laser drilling, microblasting, or ultrasonic drilling. Other techniques of forming through-holes include various etching techniques and water-jet drilling. Laser drilling of cylindrical holes generally occurs through melting and vaporization of the substrate material, e.g., ablation, through absorption of energy from a focused laser beam. Depending on the direction of the laser energy, the laser drilled through-holes can have an inverse trapezoidal shape in a cross section. Microblasting removes material by driving a high velocity fluid stream of air or inert gases of fine abrasive particles, usually about 0.001 inches (0.025 mm) in diameter. Ultrasonic drilling involves using high frequency vibrations to hammer a bit through materials. At least two through-holes are formed for every biochip—an inlet and an outlet. More than two through-holes may be used for different inlet fluids or if the biochip performs separation of the analyte and more than one outlet is used. FIG. 7 is a cross section diagram of a fluid substrate 301 having two through-holes 701 and 703 formed in operation 209.

In operation 211, the bonding material is activated. As discussed, the method of activation depends on the bonding material. Activation may include exposure to plasma, gas/vapors, fluid, heat, or radiation. Because the fluid substrate is separate from the sensing wafer and does not include biological materials, the bonding material activation is not limited to low energy methods. In the example of PSQ, an oxygen plasma creates breaks bonds on the PSQ surface and creates dangling bonds which readily adhere to a silicon oxide, e.g., silicon dioxide, a thin layer of which is always present on a silicon wafer exposed to ambient conditions. However, some care is taken to not damage the one or more surface modification layers.

In operation 213, a sensing wafer having two or more modified surface patterns having different surface chemistries is provided. The sensing wafer may be formed by the same entity performing method 200, for example, a semiconductor manufacturer or a semiconductor foundry, or by a different entity, for example, a medical device company or a semiconductor packaging facility. A summary of the sensing wafer formation is presented to provide context for the present disclosure. A sensing wafer is usually a silicon substrate with a variety of biosensors formed in or on the silicon. One example biosensor is a BioFET, which may have a sensing surface on the front of the gate or on the back of the gate. A sensing wafer with backside BioFETs have BioFETs connected by an interconnect structure to electrodes on the back side of the sensing wafer. The front side of the sensing wafer would include sensing surfaces on the back side of the gates of the BioFETs. The sensing surfaces are patterned. The BioFETs are formed directly on the sensing wafer using CMOS fabrication processes. Other biosensors on the sensing wafer may include electrodes, surface plasmon resonance sensor, potentiometric biosensor, and other biosensors that are compatible with conventional CMOS processes. Additional devices may also be formed directly on the sensing wafer using conventional CMOS processes, for example, various MEMS devices may include resonistors, actuators, valves, accelerometers, pressure sensor, heater, cooler, among others.

In operation 215, the sensing wafer and the fluidic substrate is bonded via the bonding material pattern at a temperature less than about 75 degrees Celsius, in some embodiments. The fluidic substrate is aligned with the sensing wafer and placed together. In some embodiments, pressure is applied to ensure even bonding. In other embodiments, one or more of the fluidic substrate and the sensing wafer is heated. However, because the surface modification layers and the sensing surface may be sensitive to excessive heat, the substrate temperature may be less than about 75 degrees Celsius, e.g., about room temperature.

After the fluidic substrate and the sensing wafer are bonded, the combined workpiece may undergo further processing before the workpiece is diced into individual biochips. Further processing may include testing, wafer-level packaging, and depositing protective layers. During dicing, the workpiece is cut along scribe lines between the biochips. A sufficient width of bonding material is used in the scribe line area to ensure that the separated biochips remain sealed.

Some embodiments according to the method 200 of FIG. 2A disclose a microfluidic channel formed in the fluidic substrate. The microfluidic channels are formed by dry or wet etching. The microfluidic channels may be about 100 microns in depth. Because the first surface modification layer and the bonding material deposition may be deposited using semiconductor tools with different substrate holding mechanisms, whether the fluidic substrate has through-holes may limit the application of the first surface modification layer or the bonding material. In some embodiments, the first surface modification layer is deposited in a blanket manner over the microfluidic channel and the fluidic substrate before the jet printing or other selective deposition of the bonding material on the first surface modification layer and then the through-holes are formed. In other embodiments, the through-holes are formed before depositing the bonding material, if the jet printer can handle fluidic substrates having through-holes. In still other embodiments, the through holes are formed before depositing the first surface modification layer. Earlier formation of the through holes ensures that less laser drilling by-products remains in the microfluidic channels.

In certain embodiments, the bonding material is not compatible with the surface modification layers. The first surface modification layer may be patterned so that the bonding material deposited does not overlap the surface modification layer. Whether the surface modification layer is patterned or not, the through holes may be formed at any stage according to the handling capabilities of the tools involved.

In other embodiments, the microfluidic channels are not formed on the fluidic substrate, but rather on the sensing wafer. The surface modification layer is deposited in a blanket manner on the fluidic substrate and the bonding material may be deposited using a photolithographic lift-off process before the through holes are formed. In the lift-off process, a photoresist is patterned on the surface modification layer creating a pattern of exposed surface modification layer. The bonding material is then deposited over the fluidic substrate, over both the exposed pattern and the photoresist. The photoresist pattern is then removed, or lifted-off, and the portion of the bonding material deposited on the exposed portion of the surface modification layer remains. In one embodiment where the bonding material is incompatible or does not adhere to the surface modification layer, an etch may remove the exposed surface modification layer from the fluidic substrate before the bonding material is deposited. In another embodiment, the through holes may be formed before the photoresist pattern with the bonding material is lifted-off. Of course, bonding material may also be printed using a jet printing just as in other embodiments.

In some embodiments, washing steps may be used to remove unbounded or excess bonding material instead of the lift-off process. Bonding material may be selectively bounded by a number of methods including selective activation through photolithography. Unbounded or excess bonding material may then be washed off the fluidic substrate or the sensing wafer while the bounded bonding material remains.

In still other embodiments, the surface modification layer and the bonding material may be the same material. Examples include PSQ and APTES. The surface modification layer/bonding material is deposited on the fluidic substrate and coated with a photoresist or another protective layer for the through-hole formation. Once the through-holes are formed, the protective layer, or the photoresist is removed.

Another aspect of the present disclosure pertains to embodiments where the microfluidic channels are formed on the fluidic substrate as opposed to formed in the fluidic substrate. FIGS. 2B and 8-9, 10A-10I, and 11A-11G the method 250 and cross-section diagrams in accordance with this aspect of the present disclosure. Because some of the operations of method 250 are very similar or the same as the operations of method 200, the similarities are not discussed in detail and only differences are emphasized. In operation 251 of method 250 in FIG. 2B, a first substrate is provided. The first substrate may be the fluidic substrate or the sensing wafer with a number of biosensors formed thereon.

Figure 8:
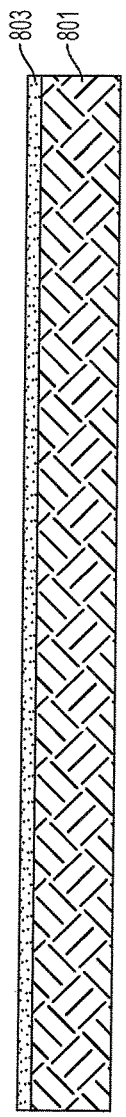
Figure 9:
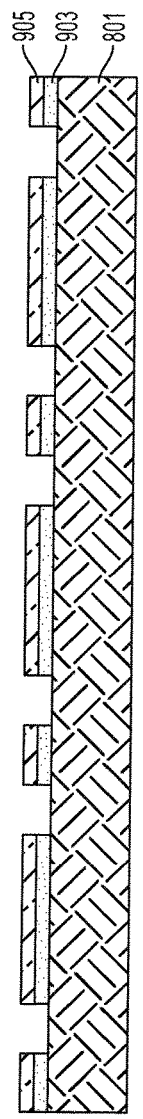

In operation 253 a first surface modification layer is patterned on the first substrate. The first surface modification layer is deposited on the first substrate and then patterned using a photolithographic process. FIG. 8 shows a first substrate 801 with a first surface modification layer 803 deposited thereon. FIG. 9 shows the same first substrate 801 with a patterned first surface modification layer 903 and a patterned photoresist layer 905 over the patterned surface modification layer 903. The photoresist is deposited over the first surface modification layer 803 and exposed to a light pattern. A portion of the photoresist is then removed. In some embodiments, the first surface modification layer may be removed along with the photoresist. For example, HMDS as the first surface modification layer may be removed by developer AZ400K along with photoresist AZ5214-E. In other embodiments, the first surface modification layer may be etched using the photoresist as an etch mask.

Figure 10A:
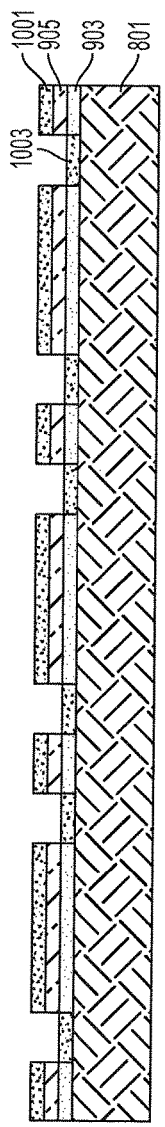
Figure 10B:
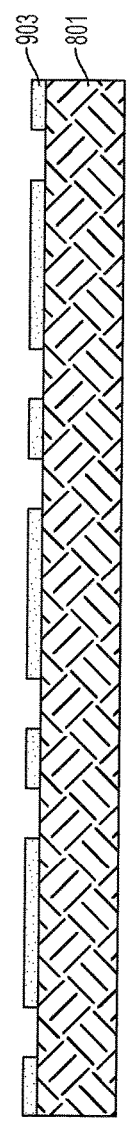
Figure 10C:
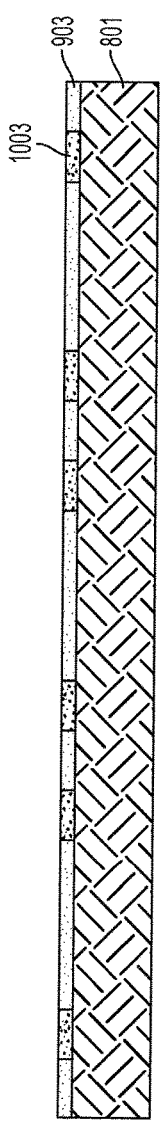

In operation 255, a second surface modification layer is patterned on the first substrate in the first surface modification layer or over the first surface modification layer. As shown in FIG. 10A, in some embodiments, a second surface modification layer is deposited over the patterned photoresist and first surface modification layer of FIG. 9. The second surface modification layer portion 1003 coats the exposed first substrate 801 between the patterned photoresist 905 and first surface modification layer 903. Another second surface modification layer portion 1001 coats the patterned photoresist 905 The patterned photoresist 905 and the second surface modification layer 1001 over the patterned photoresist are then removed in a lift-off operation to result in the cross section of FIG. 10C. FIG. 10C shows the first substrate 801 with a layer of first surface modification layer 903 and second surface modification layer 1003. In other embodiments, as shown in FIG. 10B, the photoresist pattern 905 of FIG. 9 is removed to result in simply the first substrate 801 with a patterned first surface modification layer 903 over it. The second surface modification layer may be selectively deposited over the patterned first surface modification layer to result in the cross section of FIG. 10C when the first surface modification layer and the second surface modification layer are insoluble and unwettable with each other. In other words, the two surface modification layers have self-assembled surface chemistry. One example of such combination is HMDS as one of the surface modification layers and APTES and as the other surface modification layer.

Referring back to method 250 of FIG. 2B, the forming of patterned surface modification layers may be repeated in loop 271 for additional surface modification layers. Additional surface modification layers may be built over existing surface modification layers or openings may be patterned and deposited into. Additional surface modification layers may include metal and metal oxide layers, silicon oxide, silicon nitride, and other suitable surface modification layers.

Figure 10D:
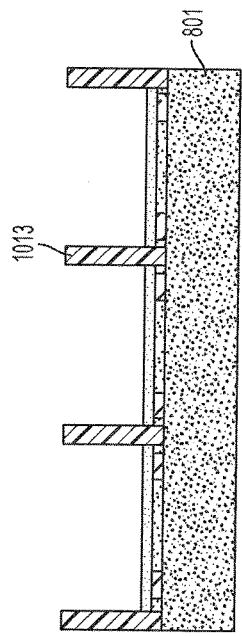

In operation 257, a photoresist is patterned on the first substrate. This operation forms a pattern for the sidewall that lines the microfluidic channels and wells. The photoresist may be patterned in a similar process as operation 253, if the openings are formed in the first surface modification layer. The photoresist is deposited and exposed to a light pattern. A portion of the photoresist is removed during the developing process. In operation 259, a portion of the first surface modification layer exposed through the patterned photoresist is removed. In some embodiments, during developing, the developer may also remove the underlying first surface modification layer to result in cross section of FIG. 10D. FIG. 10D shows the first substrate 801 with patterned first surface modification layer 903, second surface modification layer 1003 and patterned photoresist 1005. In other embodiments, the first surface modification layer is removed by etching or other chemical means using the patterned photoresist as a mask to result in the cross section of FIG. 10D.

Figure 10E:
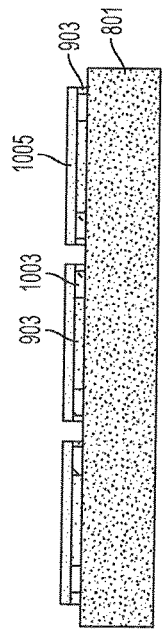

Referring back to FIG. 2B, in operation 261 a sidewall structure material is deposited over the first substrate. The sidewall structure material may be a photoresist, a silicone, a thermoplastic material, or insulator. The sidewall structure material is deposited sufficiently thick to form the sidewalls of microfluidic channels. According to various embodiments, the sidewalls may be 100 microns or taller. Photoresist material can be designed to have different surface viscosities and use different deposition process parameters to form a relatively uniform film over the substrate. One such example is SU-8. Silicone material may be molded and shaped to various shapes and sizes. Once hardened, silicone material can provide a hydrophobic or hydrophilic surface as fluid channels. In some embodiments, a silicone material polydimethylsiloxane (PDMS) is patterned by a soft lithography process. The PDMS is poured over a wafer having desired sidewall shapes etched into it and hardened. The PDMS is then removed and sealed to a glass substrate by activating the PDMS surface using RF plasma. In other embodiments, the PDMS is molded using compression molding or injection molding directly on the first substrate. Thermoplastic materials can also be patterned using soft lithography or molding processes. Suitable thermoplastic material includes poly(methyl methacrylate) (PMMA), polycarbonate (PC), and polyimide (PI). Various insulators may be deposited and patterned using semiconductor processes. For example, silicon oxide, silicon nitride, or various commonly used insulators in semiconductor processing may be used. The sidewall structure material may have more than one layers. In some embodiments, the first layer adds thickness while the second or subsequent layers add desirable properties such as adhesion to another substrate and surface property. FIG. 10E shows a first substrate 801, a patterned first surface modification layer 903 and second surface modification layer 1003 over the substrate, a patterned photoresist 1005 over the surface modification layers 903 and 1003, and a sidewall structure material 1007 over the first substrate 801 and the patterned photoresist 1005.

Figure 10F:
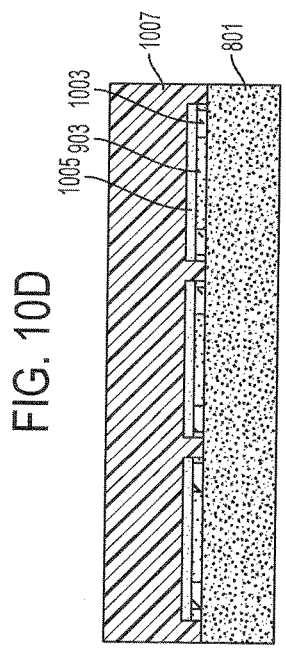

Referring back to FIG. 2B, in operation 263 through-holes are formed in the first substrate. The through-holes are formed using processes similar to those discussed in association with operation 209 of FIG. 2A with consideration to the sidewall structure material. Depending on the material properties of the sidewall structure material, a different through-hole making process may be used. In one example, if the sidewall structure material is PMMA and the through-holes are formed using laser, then an annealing step may be required. FIG. 10F shows a cross section of the partially fabricated workpiece having through-holes 1009.

Figure 10G:
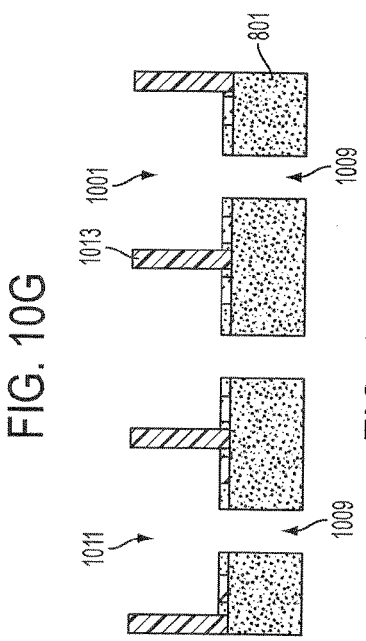
Figure 10H:
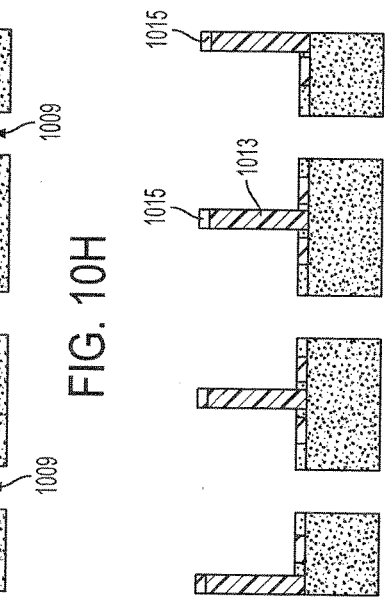

Referring back to FIG. 2B, in operation 265 the sidewall structure material is patterned. Depending on the material used for the sidewall structure material, a molded piece or a blanket deposition may be formed on the first substrate in operation 261. In one example, the sidewall structure material is a photoresist, for example SU-8, which may be patterned by exposing and developing the photoresist. Other patterning options include laser (low power), electron beam, deep UV light, dry or wet etching, and polishing. FIG. 10H shows a cross section of the partially fabricated workpiece having through-holes 1009, sidewalls 1013 and channels 1011. The patterned photoresist is also removed at this stage or at a later stage, for example, by oxygen plasma after the bonding material is printed.

In some embodiments, the sidewall structure material is patterned before the through-hole formation. The patterned photoresist 1005 is used as an etch stop layer. FIG. 10G shows a patterned sidewalls 1013 on a first substrate 801 before the through-holes are formed. From the cross section of FIG. 10G, the through-holes would then be formed as shown in FIG. 10H.

Figure 10I:
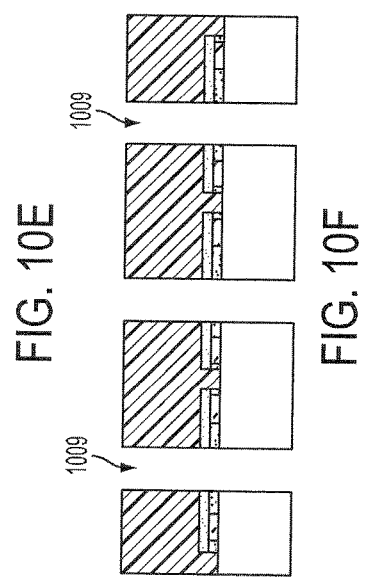

Referring back to FIG. 2B, in operation 267 a bonding material layer is formed. The bonding material layer may be formed using processes similar to operation 207 of FIG. 2A. FIG. 10I shows a cross section of the partially fabricated workpiece having bonding material layer on the top of the sidewalls 1013.

Referring back to FIG. 2B, in operation 269 the first substrate to bonded to a second substrate via the bonding material layer. This operation is similar to operation 215 of FIG. 2A. The second substrate may be a sensing wafer if the first substrate is a fluidic substrate. The second substrate may be a fluidic substrate if the first substrate is a sensing wafer. After bonding, a workpiece similar to the biochip 100 of FIG. 1 is formed.

As discussed, loop 271 of FIG. 2B may be used to add additional surface modification layer on the first substrate. FIGS. 11A to 11G shows such embodiments. After the first surface modification layer and the second surface modification layer are formed, a third surface modification layer is deposited by liquid phase coating followed by lithography or UV curing. In one example, a PEG hydrogel may be UV cured after liquid phase deposition to form the third surface modification layer 1101 of FIG. 11A. FIG. 11A shows the first substrate 801 with a layer of first surface modification layer 903, second surface modification layer 1003 in openings of the first surface modification layer 903, and a third surface modification layer 1101 over the second surface modification layer 1003. The third surface modification layer may be a self-assembled layer, i.e., it is selectively deposited if the surface property of the first surface modification layer is chosen so that the third surface modification layer in liquid phase does not adhere to the first surface modification layer. In the example of PEG hydrogel, the hydrogel does not adhere to a hydrophobic surface if HDMS is used as the first surface modification layer. Various PEG hydrogel may be selected for a its terminal functional group. For example, diacrylate terminated PEG (PEG-DA) can be used for binding with specific peptides or proteins.

After the third surface modification layer is formed, the process proceeds through operations 257 to 265 as described in association with FIGS. 10D to 10H. FIG. 11B corresponds to FIG. 10D; FIG. 11C corresponds to FIG. 10E; FIG. 11D corresponds to FIG. 10F; FIG. 11E corresponds to FIG. 10G; and FIG. 11F corresponds to FIG. 10H. Referring back to FIG. 2B, in operation 267 where a bonding layer is formed on the sidewalls. In the embodiment having a third surface modification layer, the bonding material may also be deposited on the third surface modification layer depending on the bonding material and method of deposition. For example, if a liquid or vapor phase deposition is used, the liquid or vapor would deposit on all surface on which it would adhere. As shown in FIG. 11G, if the first surface modification layer 903 is hydrophobic as the sidewall 1013, then the bonding material 1103 would also deposit onto the third surface modification layer 1101. In some embodiments, the bonding material may also deposit in the sidewalls of the through-holes. According to various embodiments, for bonding material APTES and third surface modification layer as PEG hydrogel, having a layer APTES does not impede biomaterial from entering and functionalizing the PEG hydrogel. As discussed, the photoresist layer over the third surface modification layer may be removed after the bonding material deposition in some embodiments. In such case the bonding material would not deposit on the third surface modification layer.

One aspect of the present disclosure pertains to a biochip which includes a substrate, where the substrate includes at least one hole extending from a first surface of the substrate to a second surface of the substrate opposite the first surface, and where the substrate comprises a microfluidic channel pattern. The biochip further includes a surface modification layer over the substrate. Additionally, the biochip includes a sensing wafer bonded to the substrate, where the sensing wafer has one or more modified surface patterns having different surface properties from each other.

Another aspect of the present disclosure pertains to a biochip including a fluidic substrate having at least one hole extending therethrough. Additionally, the biochip includes a patterned surface modification layer over the fluidic substrate. Moreover, the biochip includes a sensing wafer over the fluidic substrate, where the sensing wafer comprises one or more modified surface patterns having different surface properties from each other. Furthermore, the biochip includes a bonding material between the fluidic substrate and the sensing wafer.

In yet another aspect, the present disclosure pertains to biochip including a fluidic substrate, where the fluidic substrate has at least one hole extending from a first surface of the fluidic substrate to a second surface of the fluidic substrate opposite the first surface. Additionally, the biochip includes a surface modification layer over sidewalls of the at least one hole, wherein the surface modification layer includes amino-silane, hexamethyldisilazane (HMDS), agar, hydrogel, or chemistries with thiol functional groups. Moreover, the biochip includes a sensing wafer over the fluidic substrate.

In describing one or more of these embodiments, the present disclosure may offer several advantages over prior art devices. In the discussion of the advantages or benefits that follows it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:

1. A biochip comprising:
    a substrate, wherein the substrate comprises at least one hole extending from a first surface of the substrate to a second surface of the substrate opposite the first surface and a plurality of cavities, and wherein the substrate comprises a microfluidic channel pattern configured to connect the at least one hole to each cavity of the plurality of cavities;
    a plurality of surface modification layers over the substrate; and
    a sensing wafer bonded to the substrate, wherein the sensing wafer has a plurality of modified surface patterns, wherein a first modified surface pattern of the plurality of modified surface patterns has different surface properties from a second modified surface pattern of the plurality of modified surface patterns.

2. The biochip of claim 1, further comprising a bonding material between the substrate and the sensing wafer.

3. The biochip of claim 2, wherein the bonding material comprises poly(phenylmethyl)silsesquioxane (PSQ) or 3-aminopropyl triethoxysilane (APTES).

4. The biochip of claim 2, wherein the bonding material is configured to be non reactive with analyte, bioreceptors, or a testing fluid.

5. The biochip of claim 1, wherein a first surface modification layer of the plurality of surface modification layers comprises amino-silane, hexamethyldisilazane (HMDS), agar, hydrogel, or chemistries with thiol functional groups.

6. The biochip of claim 1, wherein at least one surface modification layer of the plurality of surface modification layers is over sidewalls of the at least one hole.

7. A biochip comprising:
a fluidic substrate having at least one hole extending therethrough;
a patterned surface modification layer over the fluidic substrate;
a sensing wafer over the fluidic substrate, wherein the sensing wafer comprises a plurality of modified surface patterns, wherein a first modified surface pattern of the plurality of modified surface patterns has different surface properties from a second modified surface pattern of the plurality of modified surface patterns; and
a bonding material between the fluidic substrate and the sensing wafer.

8. The biochip of claim 7, wherein the bonding material comprises poly(phenylmethyl)silsesquioxane (PSQ) or 3-aminopropyl triethoxysilane (APTES).

9. The biochip of claim 7, wherein the fluidic substrate is aligned with the sensing wafer.

10. The biochip of claim 7, wherein the patterned surface modification layer comprises amino-silane, hexamethyldisilazane (HMDS), agar, hydrogel, or chemistries with thiol functional groups.

11. The biochip of claim 7, wherein the patterned surface modification layer is over sidewalls of the at least one hole.

12. The biochip of claim 7, wherein the fluidic substrate is configured to be non reactive with an analyte.

13. The biochip of claim 7, wherein the bonding material is configured to be non reactive with an analyte, bioreceptors, or a testing fluid.

14. A biochip comprising:
a fluidic substrate, wherein the fluidic substrate has at least one hole extending from a first surface of the fluidic substrate to a second surface of the fluidic substrate opposite the first surface;
a surface modification layer over sidewalls of the at least one hole, wherein the surface modification layer comprises amino-silane, hexamethyldisilazane (HMDS), agar, hydrogel, or chemistries with thiol functional groups; and
a sensing wafer spaced from the fluidic substrate.

15. The biochip of claim 14, wherein the sensing wafer comprises one or more modified surface patterns, and the modified surface patterns have different surface properties from each other.

16. The biochip of claim 14, further comprising a bonding material between the substrate and the sensing wafer.

17. The biochip of claim 16, wherein the bonding material comprises poly(phenylmethyl)silsesquioxane (PSQ) or 3-aminopropyl triethoxysilane (APTES).

18. The biochip of claim 16, wherein the bonding material is non reactive with an analyte, bioreceptors, or a testing fluid.

19. The biochip of claim 14, wherein the fluidic substrate is aligned with the sensing wafer.

20. The biochip of claim 14, wherein the fluidic substrate has a thickness of at least 100 microns (μm).

\* \* \* \* \*